United States Patent [19]
Sowerby

[11] Patent Number: 5,824,626
[45] Date of Patent: Oct. 20, 1998

[54] PROCESS FOR PREPARING TRITHIANES AND PHOSPHORUS ACID AND/OR THIOPHOSPHORUS ACID DERIVATIVES

[75] Inventor: Roger L. Sowerby, Concord, Ohio

[73] Assignee: The Lubrizol Corporation, Wickliffe, Ohio

[21] Appl. No.: 910,967

[22] Filed: Jul. 9, 1992

Related U.S. Application Data

[63] Continuation-in-part of Ser. No. 640,173, Jan. 11, 1991, abandoned.

[51] Int. Cl.$^6$ .................... C10M 135/34; C10M 141/10
[52] U.S. Cl. ............................... 508/300; 508/438
[58] Field of Search ................... 252/32.7 E, 45, 252/46.6; 508/300, 438

[56] References Cited

U.S. PATENT DOCUMENTS

| | | | |
|---|---|---|---|
| 2,213,804 | 9/1940 | Lincoln et al. | 252/46.6 |
| 2,531,129 | 11/1950 | Hook et al. | 252/46.6 |
| 2,948,682 | 8/1960 | Crosby et al. | 252/46.6 |
| 3,159,664 | 12/1964 | Bartlett | 252/46.6 |
| 3,192,162 | 6/1965 | Bartlett et al. | 252/46.6 |
| 3,644,206 | 2/1972 | Braid | 252/46.6 |

*Primary Examiner*—Jacqueline V. Howard
*Attorney, Agent, or Firm*—James L. Cordek; William J. Connors; Joseph P. Fischer

[57] ABSTRACT

Trithiane and phosphorus and/or thiophosphorus acid derivatives are described which are useful as extreme pressure compositions. The process comprises a reaction product obtained by reacting (A) an aldehyde of the structure

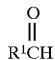

wherein R is a hydrocarbyl group containing from 1 to about 18 carbon atoms with (B) a phosphorus acid of the structure

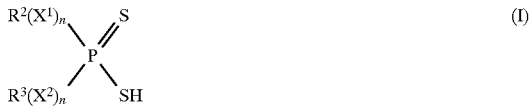

wherein $R^2$ and $R^3$ are each independently a hydrocarbyl group containing from 1 to about 30 carbon atoms, $X^1$ and $X^2$ are each independently oxygen or sulfur and n is independently zero or one in the presence of a lubricating base oil.

A neutralizing agent, component (C), may be reacted with the phosphorus acid and/or thiophosphorus acid intermediate formed by the reaction of components (A) and (B).

32 Claims, No Drawings

PROCESS FOR PREPARING TRITHIANES AND PHOSPHORUS ACID AND/OR THIOPHOSPHORUS ACID DERIVATIVES

This is a continuation-in-part of application Ser. No. 07/640,173 filed on Jan. 11, 1991, now abandoned.

FIELD OF THE INVENTION

This invention relates to a process for the preparation of trithianes and phosphorus acid and/or thiophosphorus acid derivatives. More particularly, the invention relates to the process of the above preparation as an automotive extreme pressure (EP) additive.

BACKGROUND OF THE INVENTION

When hypoid gears, worm gears, heavy duty bearings, planetary automatic shifts and the like are used under conditions of high pressure and high rubbing velocities, special types of extreme pressure lubricants must be provided in order to reduce the wear upon such moving parts. Extreme pressure lubricants are likewise important in cutting and drawing operations where the oil must withstand high pressures encountered under those conditions of use.

U.S. Pat. No. 2,213,804 (Lincoln et al, Sep. 3, 1940) relates to lubricating oils that contain an addition agent improving its film strength and oiliness. The addition agents are stable, heterocyclic sulfur compounds and hydrocarbon lubricants.

U.S. Pat. No. 2,337,868 (Burwell et al, Dec. 28, 1943) relates to lubricating compositions of lubricating oil and relatively small amounts of thio-alkyl derivatives of oxygenated saturated aliphatic compounds (alcohols, alcohol-ketones, ketones, hydroxy carboxylic acids, and alkyl esters of such acids, of relatively high molecular weights) derived from mineral hydrocarbonaceous mixtures (e.g., petroleum oils and/or waxes) by the controlled partial oxidation of the latter in liquid phase.

U.S. Pat. No. 2,712,526 (McDermott, Jul. 5, 1955) relates to salts formed by reacting thialdine or its homologs with sulfur-containing acids, such as sulfurized carboxylic acids, thiocarboxylic acids and the thio acids of phosphorus. These salts are effective antioxidants for hydrocarbon products liable to corn, especially mineral lubricating oils.

U.S. Pat. No. 2,900,392 (Remes et al, Aug. 18, 1959 relates to the preparation of sulfur-containing heterocyclic compounds. More specifically, this reference is concerned with the synthesis of heterocyclic hydrocarbons having two sulfur atoms in a hetatomic ring.

SUMMARY OF THE INVENTION

The present invention is a process for preparing an extreme pressure additive comprising a reaction product obtained by reacting (A) an aldehyde of the structure

$$R^1CH$$

wherein $R^1$ is a hydrocarbyl group containing from 1 to about 18 carbon atoms with (B) a phosphorus acid of the structure

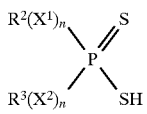

(I)

wherein $R^2$ and $R^3$ are each independently a hydrocarbyl group containing from 1 to about 30 carbon atoms, $X^1$ and $X^2$ are each independently oxygen or sulfur and n is independently zero or one in the presence of a lubricating base oil.

DETAILED DESCRIPTION OF THE INVENTION

The process for preparing the extreme pressure additive of the present invention comprises forming a trithiane and phosphorus acid and/or thiophosphorus acid derivative in the presence of a lubricating base oil.

The Lubricating Base Oil

The base oils used in preparing the additive of this invention can be natural oils or synthetic oils. Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils and halosubstituted hydrocarbon oils such as polymerized and interpolymerized olefins (e.g., polybutylenes, polypropylenes, propyleneisobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl) benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 1000, diphenyl ether of polyethylene glycol having a molecular weight of about 500–1000, diethyl ether of polypropylene glycol having a molecular weight of about 1000–1500, etc.) or mono- and polycarboxylic esters thereof, for example, the acetic acid esters, mixed $C_3$–$C_8$ fatty acid esters, or the $C_{13}$Oxo acid diester of tetraethylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)- sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-hexyl)silicate, tetra-(p-tert-butyl-phenyl)silicate, hexyl-(4-methyl-2-pentoxy) disiloxane, poly(methyl)siloxanes, poly(methyl-phenyl) siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the concentrates of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Trithiane and Phosphorus Acid and/or Thionhosphorus Acid Derivative

Contained within the lubricating base oil are a trithiane and phosphorus acid and/or thiophosphorus acid derivative. These are prepared by reacting (A) an aldehyde $$\underset{R^1CH}{\overset{O}{\|}}$$

wherein $R^1$ is a hydrocarbyl group containing from 1 to about 18 carbon atoms, preferably 1 to about 12 carbon atoms and most preferably from 1 to about 8 carbon atoms with (B) a phosphorus acid of the structure

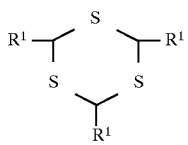  (I)

wherein $R^2$ and $R^3$ are each independently hydrocarbyl groups containing from 1 to about 30 carbon atoms, preferably from 1 to about 18 carbon atoms and most preferably from 1 to about 12 carbon atoms, $X^1$ and $X^2$ are each independently oxygen or sulfur, and n is independently zero or one.

The phosphorus acid and/or thiophosphorus acid intermediate so formed may then be reacted with (C) a neutralizing agent comprising a metal overbased composition, an amine, metal oxides or hydroxides.

When the (A):(B) molar ratio is 1:1:, it is theorized that components (A) and (B) react to form a trithiane and component (D)

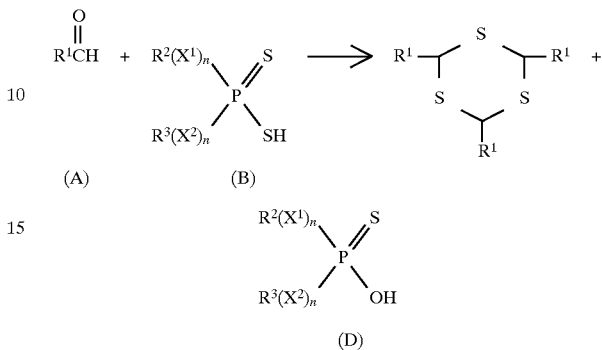

When the (A):(B) molar ratio is 2:1, the following trithiane and component (D) is formed:

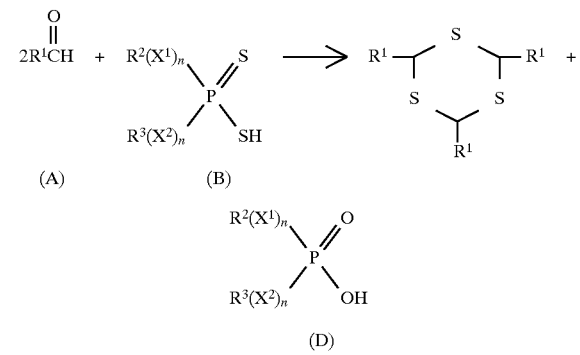

The trithiane

is formed from the trimerization of

The thioaldehyde

is one of the products of reaction of components (A) and (B) with the other reaction product being component (D). The thioaldehyde

trimerizes under the reaction conditions to give a trithiane.

The neutralizing agent is reacted with component (D) to give a salt. This salt with the accompanying trithiane along with a lubricating oil forms the extreme pressure additive of this invention.

An illustrative but not exhaustive list of aldehydes having utility in this invention as component (A) are formaldehyde, acetaldehyde, propionaldehyde, n-butyraldehyde, isobutyraldehyde, n-valeraldehyde, α-methylbutyraldehyde, β-methylbutyraldehyde, n-caproaldehyde, α-methylvaleraldehyde, β-methylvaleraldehyde, heptaldehyde, ethylhexavaleraldehyde, lauraldehyde, myristaldehyde, palmitaldehyde, stearaldehyde, benzaldehyde, p-nitrobenzaldehyde, p-tolualdehyde, salicylaldehyde, phenylacetaldehyde, p-hydroxybenyaldehyde, and anisaldehyde. Preferred are isobutyraldehyde and 2-ethylhexanaldehyde.

Typical phosphorus-containing acids (B) from which the additives of this invention can be made are known. Illustrative examples of some preferred phosphorus- and sulfur-containing acids are:

1. Dihydrocarbylphosphinodithioic acids, such as amylphosphinodithioic acid, corresponding to the formula

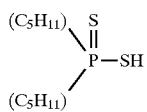

2. S-hydrocarbyl hydrogen hydrocarbylphosphonotrithioates, such as S-amyl hydrogen amylphosphonotrithioate, corresponding to the formula

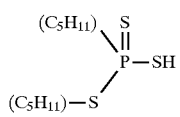

3. O-hydrocarbyl hydrogen hydrocarbylphosphonodithioates, such as O-amyl hydrogen amylphosphonodithioate, corresponding to the formula

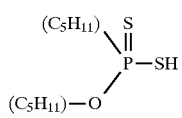

4. S-S-dihydrocarbyl hydrogen phosphorotetrathioates, such as diamyl hydrogen phosphorotetrathioate, corresponding to the formula

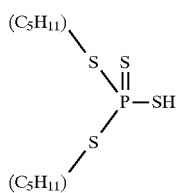

5. O,S-dihydrocarbyl hydrogen phosphorotrithioates, such as O,S-diamyl hydrogen phosphorotrithioate, corresponding to the formula

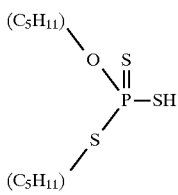

6. O,O-dihydrocarbyl hydrogen phosphorodithioates, such as O,O-diamyl hydrogen phosphorodithioate, corresponding to the formula

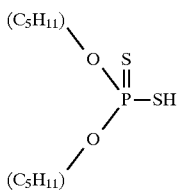

Preferred acids of the formula

are readily obtainable from the reaction of phosphorus pentasulfide ($P_2S_5$) and an alcohol or a phenol. The reaction involves mixing at a temperature of about 20° to about 200° C., 4 moles of the alcohol or a phenol with one mole of phosphorus pentasulfide. Hydrogen sulfide is liberated in this reaction. The oxygen-containing analogs of these acids are conveniently prepared by treating the preferred dithioic acid with water or steam which, in effect, replaces one or both of the sulfur atoms.

The terminology of "hydrocarbon-based radical" as used herein, ("herein" includes the appended claims) is used to define a substantially saturated monovalent radical derived from a hydrocarbon by removal of a hydrogen from a carbon atom of the hydrocarbon. This carbon atom is directly connected to the remainder of the molecule. These hydrocarbon-based radicals are derived from aliphatic hydrocarbons, cyclo-aliphatic hydrocarbons, aromatic hydrocarbons, mixed aliphatic-cyclo-aliphatic hydrocarbons, mixed aliphatic aromatic hydrocarbons, and mixed cyclo-aliphatic-aromatic hydrocarbons. Therefore, these hydrocarbon-based radicals would be referred to as aliphatic-based radicals, cyclo-aliphatic-based radicals, etc. The base hydrocarbons from which these radicals are derived may contain certain non-reactive or substantially non-reactive polar or non-hydrocarbon substituents.

The terminology "substantially saturated" as used herein is intended to define radicals free from acetylenic unsaturation (—C≡C—) in which there is not more than one ethylenic linkage (—C=C—) for every 10 carbon-to-carbon (preferably 20) covalent bonds. The so-called "double bonds" in the aromatic ring (e.g., benzene) are not to be considered as contributing to unsaturation with respect to the terminology "substantially saturated". Usually there will be no more than an average of one ethylenic linkage per substantially saturated monovalent radical as described herein. Preferably, (with the exception of aromatic rings) all the carbon-to-carbon bonds in a substantially saturated radical will be saturated linkages; that is, the radical will be free from acetylenic and ethylenic linkages.

The hydrocarbon-based radicals may contain certain non-reactive or substantially non-reactive polar or nonhydrocarbon substituents which do not materially interfere with the reactions or compositions herein, as will be recognized by those skilled in the art. Representative non-hydrocarbon or polar substituents include halo substituents, such as chloro, fluoro, bromo and iodo; nitro; lower alkoxy, such as butoxy and hexyloxy; lower alkyl thio, such as pentylthio and heptylthio; hydroxy; mercapto; and the like. As a general rule, and particularly when the additives of this invention are to be used as lubricant additives, the degree of substitution and nature of the substituent of the hydrocarbon-based radical is such that the predominantly hydrocarbon character of the radical is not destroyed. Thus, in view of this requirement, these radicals normally have no more than four substituents per radical, and usually, not more than one substituent for every 10 carbon atoms in the radical. Preferably, the hydrocarbon-based radical is a purely hydrocarbyl (i.e., a hydrocarbon radical containing only carbon and hydrogen atoms).

Neutralizing Agent, Component (C)

The neutralizing agent, component (C) is reacted with component (D) to produce a salt. The neutralizing agent (C) is a metal overbased composition, an amine, a metal oxide or metal hydroxide.

The Metal Overbased Composition

Overbased salts of organic acids are widely known to those of skill in the art and generally include metal salts wherein the amount of metal present in them exceeds the stoichiometric amount. Such salts are said to have conversion levels in excess of 100% (i.e., they comprise more than 100% of the theoretical amount of metal needed to convert the acid to its "normal" "neutral" salt). Such salts are often said to have metal ratios in excess of one (i.e., the ratio of equivalents of metal to equivalents of organic acid present in the salt is greater than that required to provide the normal or neutral salt which required only a stoichiometric ratio of 1:1). They are commonly referred to as overbased, hyperbased or superbased salts and are usually salts of organic sulfur acids, organic phosphorus acids, carboxylic acids, phenols or mixtures of two or more of any of these. As a skilled worker would realize, mixtures of such overbased salts can also be used.

The terminology "metal ratio" is used in the prior art and herein to designate the ratio of the total chemical equivalents of the metal in the overbased salt to the chemical equivalents of the metal in the salt which would be expected to result in the reaction between the organic acid to be overbased and the basically reacting metal compound according to the known chemical reactivity and stoichiometry of the two reactants. Thus, in a normal or neutral salt the metal ratio is one and in an overbased salt the metal ratio is greater than one.

The overbased salts used as (C) in this invention usually have metal ratios of at least about 2:1. Typically, they have ratios of at least about 12:1. Usually they have metal ratios not exceeding about 40:1. Typically salts having ratios of about 12:1 to about 20:1 are used.

Basic metal compounds used to make these overbased salts are usually an alkali or alkaline earth metal compound (i.e., the Group IA, IIA, and IIB metals excluding francium and radium and typically excluding rubidium, cesium and beryllium) although other basic metal compounds can be used. Compounds of Ca, Ba, Mg, Na and Li, such as their hydroxides and alkoxides of lower alkanols are usually used as basic metal compounds in preparing these overbased salts but others can be used as shown by the prior art incorporated by reference herein. Overbased salts containing a mixture of ions of two or more of these metals can be used in the present invention.

These overbased salts can be of oil-soluble organic sulfur acids such as sulfonic, sulfamic, thiosulfonic, sulfinic, sulfenic, partial ester sulfuric, sulfurous and thiosulfuric acid. Generally they are salts of carboxylic or aliphatic sulfonic acids.

The carbocylic sulfonic acids include the mono- or polynuclear aromatic or cycloaliphatic compounds. The oil-soluble sulfonates can be represented for the most part by the following formulae:

 (II)

 (III)

In the above formulae, M is either a metal cation as described hereinabove or hydrogen; T is a cyclic nucleus such as, for example, benzene, naphthalene, anthracene, phenanthrene, diphenylene oxide, thianthrene, phenoxazine, diphenylene sulfide, phenothiazine, diphenyl oxide, diphenyl sulfide, diphenylamine, cyclohexane, petroleum naphthenes, decahydro-naphthalene, cyclopentane, etc.: $R_x$ in Formula II is an aliphatic group such as alkyl, alkenyl, alkoxy, alkoxyalkyl, carboalkoxyalkyl, etc; x is at least 1, and $R_x$+T contains a total of at least about 15 carbon atoms, $R^4$ in Formula III is an aliphatic radical containing at least about 15 carbon atoms and M is either a metal cation or hydrogen. Examples of type of the $R^4$ radical are alkyl, alkenyl, alkoxyalkyl, carboalkoxyalkyl, etc. Specific examples of $R^4$ are groups derived from petrolatum, saturated and unsaturated paraffin wax, and polyolefins, including polymerized $C_2$, $C_3$, $C_4$, $C_5$, $C_6$, etc., olefins containing from about 15 to 7000 or more carbon atoms. The groups T, R, and $R^4$ in the above formulae can also contain other inorganic or organic substituents in addition to those enumerated above such as, for example, hydroxy, mercapto, halogen, nitro, amino, nitroso, sulfide, disulfide, etc. In Formula II, x, y, z and b are at least 1, and likewise in Formula III, a, b and d are at least 1.

Specific examples of sulfonic acids useful in this invention are mahogany sulfonic acids; bright stock sulfonic acids; sulfonic acids derived from lubricating oil fractions having a Saybolt viscosity from about 100 seconds at 100° F. to about 200 seconds are 210° F.; petrolatum sulfonic acids; mono- and poly-wax substituted sulfonic and polysulfonic acids of, e.g., benzene, naphthalene, phenol, diphenyl ether, napthalene disulfide, diphenylamine, thiophene, alpha-chloronaphthalene, etc.; other substituted sulfonic acids such as alkyl benzene sulfonic acids (where the alkyl group has at least 8 carbons), cetylphenol mono-sulfide sulfonic acids, dicetyl thianthrene disulfonic acids, dilauryl beta naphthyl sulfonic acid, dicapryl nitronaphthalene sulfonic acids, and alkaryl sulfonic acids such as dodecyl benzene "bottoms" sulfonic acids.

The latter acids derived from benzene which has been alkylated with propylene tetramers or isobutene trimers to introduce 1,2,3, or more branched-chain $C_{12}$ substituents on the benzene ring. Dodecyl benzene bottoms, principally mixtures of mono-and di-dodecyl benzenes, are available as by-products from the manufacture of household detergents. Similar products obtained from alkylation bottoms formed during manufacture of linear alkyl sulfonates (LAS) are also useful in making the sulfonates used in this invention.

The production of sulfonates from detergent manufacture-by-products by reaction with, e.g., $SO_3$, is well known to those skilled in the art. See, for example, the article "Sulfonates" in Kirk-Othmer "Encyclopedia of Chemical Technology", Second Edition, Vol. 19, pp. 291 at seq. published by John Wiley & Sons, N.Y. (1969).

Other descriptions of overbased sulfonate salts and techniques for making them can be found in the following U.S. Pat. Nos. 2,174,110; 2,174,506; 2,174,508; 2,193,824; 2,197,800; 2,202,781; 2,212,786; 2,213,360; 2,228,598; 2,223,676; 2,239,974; 2,263,312; 2,276,090; 2,276,297; 2,315,514; 2,319,121; 2,321,022; 2,333,568; 2,333,788; 2,335,259; 2,337,552; 2,346,568; 2,366,027; 2,374,193; 2,383,319; 3,312,618; 3,471,403; 3,488,284; 3.595,790; and 3,798,012. These are hereby incorporated by reference for their disclosures in this regard.

Also included are aliphatic sulfonic acids such as paraffin wax sulfonic acids, unsaturated paraffin wax sulfonic acids, hydroxy-substituted paraffin wax sulfonic acids, hexapropylene sulfonic acids, tetra-amylene sulfonic acids, polyisobutene sulfonic acids wherein the polyisobutene contains from 20 to 7000 or more carbon atoms, chloro-substituted paraffin wax sulfonic acids, nitroparaffin wax sulfonic acids, etc.; cycloaliphatic sulfonic acids such as petroleum naphthene sulfonic acids, cetyl cyclopentyl sulfonic acids, lauryl cyclohexyl sulfonic acids, bis-(di-isobutyl) cyclohexyl sulfonic acids, etc.

With respect to the sulfonic acids or salts thereof described herein and in the appended claims, it is intended that the term "petroleum sulfonic acids" or "petroleum sulfonates" includes all sulfonic acids or the salts thereof derived from petroleum products. A particularly valuable group of petroleum sulfonic acids are the mahogany sulfonic acids (so called because of their reddish-brown color) obtained as a by-product from the manufacture of petroleum white oils by a sulfuric acid process.

Generally Group IA, IIA and IIB overbased salts of the above-described synthetic and petroleum sulfonic acids are typically useful in making (C) of this invention.

The carboxylic acids from which suitable overbased salts for use in this invention can be made include aliphatic, cycloaliphatic, and aromatic mono- and polybasic carboxylic acids such as the napthenic acids, alkyl- or alkenyl-substituted cyclopentanoic acids, alkyl-or alkenyl-substituted cyclohexanoic acids, alkyl- or alkenyl-substituted aromatic carboxylic acids. The aliphatic acids generally contain at least 8 carbon atoms and preferably at least 12 carbon atoms. Usually they have no more than about 400 carbon atoms. Generally, if the aliphatic carbon chain is branched, the acids are more oil-soluble for any given carbon atoms content. The cycloaliphatic and aliphatic carboxylic acids can be saturated or unsaturated. Specific examples include 2-ethylhexanoic acid, a-linolenic acid, propylene-tetramer-substituted maleic acid, behenic acid, isostearic acid, pelargonic acid, capric acid, palmitoleic acid, linoleic acid, lauric acid, oleic acid, ricinoleic acid, undecylic acid, dioctylcyclopentane carboxylic acid, myristic acid, dilauryldecahydronaphthalene carboxylic acid, stearyloctahydroindene carboxylic acid, palmitic acid, commercially available mixtures of two or more carboxylic acids such as tall oil acids, rosin acids, and the like.

A typical group of oil-soluble carboxylic acids useful in preparing the salts used in the present invention are the oil-soluble aromatic carboxylic acids. These acids are represented by the general formula:

wherein R* is an aliphatic hydrocarbon-based group of at least 4 carbon atoms, and no more than about 400 aliphatic carbon atoms, a is an integer from one to four, Ar* is a polyvalent aromatic hydrocarbon nucleus of up to about 14 carbon atoms, each X is independently a sulfur or oxygen atom, and m is an integer of from one to four with the proviso that R* and a are such that there is an average of at least 8 aliphatic carbon atoms provided by the R* groups for each acid molecule represented by Formula IV. Examples of aromatic nuclei represented by the variable Ar* are the polyvalent aromatic radicals derived from benzene, napthalene anthracene, phenanthrene, indene, fluorene, biphenyl, and the like. Generally, the radical represented by Ar* will be a polyvalent nucleus derived from benzene or naphthalene such as phenylenes and naphthylene, e.g., methyphenylenes, ethoxyphenylenes, nitrophenylenes, isopropylenes, hydroxyphenylenes, mercaptophenylenes, N,N-diethylaminophenylenes, chlorophenylenes, N,N-diethylaminophenylenes, chlorophenylenes, dipropoxynaphthylenes, triethylnaphthylenes, and similar tri-, tetra-, pentavalent nuclei thereof, etc.

The R* groups are usually hydrocarbyl groups, preferably groups such as alkyl or alkenyl radicals. However, the R* groups can contain small number substituents such as phenyl, cycloalkyl (e.g., cyclohexyl, cyclopentyl, etc.) and nonhydrocarbon groups such as nitro, amino, halo (e.g., chloro, bromo, etc.), lower alkoxy, lower alkyl mercapto, oxo substituents (i.e., =O), thio groups (i.e., =S), interrupting groups such as —NH—, —O—, —S—, and the like provided the essentially hydrocarbon character of the R* group is retained. The hydrocarbon character is retained for purposes of this invention so long as any non-carbon atoms present in the R* groups do not account for more than about 10% of the total weight of the R* groups.

Examples of R* groups include butyl, isobutyl, pentyl, octyl, nonyl, dodecyl, docosyl, tetracontyl, 5-chlorohexyl, 4-ethoxypentyl, 4-hexenyl, 3-cyclohexyloctyl, 4-(p-chlorophenyl)-octyl, 2,3,5-trimethylheptyl, 4-ethyl-5-methyloctyl, and substituents derived from polymerized olefins such as polychloroprenes, polyethylenes, polypropylenes, polyisobutylenes, ethylene-propylene copolymers, chlorinated olefin polymers, oxidized ethylene-propylene copolymers, and the like. Likewise, the group Ar* may contain non-hydrocarbon substituents, for example, such diverse substituents as lower alkoxy, lower alkyl mercapto, nitro, halo, alkyl or alkenyl groups of less than 4 carbon atoms, hydroxy, mercapto, and the like.

Another group of useful carboxylic acids are those of the formula:

wherein R*, X, Ar*, m and a are as defined in Formula II and p is an integer of 1 to 4, usually 1 or 2. Within this group, an especially preferred class of oil-soluble carboxylic acids are those of the formula:

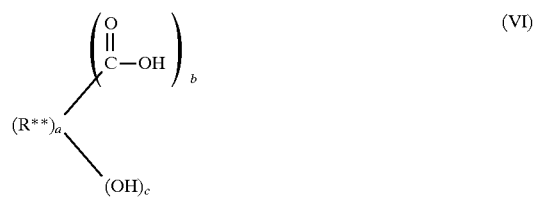

wherein R in Formula VI is an aliphatic hydrocarbon group containing at least 4 to about 400 carbon atoms, a is an integer of from 1 to 3, b is 1 or 2, c is zero, 1, or 2 and preferably 1 with the proviso that R and a are such that the acid molecules contain at least an average of about 12 aliphatic carbon atoms in the aliphatic hydrocarbon substituents per acid molecule. And within this latter group of oil-soluble carboxylic acids, the aliphatic-hydrocarbon substituted salicyclic acids wherein each aliphatic hydrocarbon substituent contains an average of at least about 16 carbon atoms per substituent and 1 to 3 substituents per molecule are particularly useful. Salts prepared from such salicyclic acids wherein the aliphatic hydrocarbon substituents are derived from polymerized olefins, particularly polymerized lower 1-mono-olefins such as polyethylene, polypropylene, polyisobutylene, ethylene/-propylene copolymers and the like and having average carbon contents of about 30 to about 400 carbon atoms.

The carboxylic acids corresponding to Formulae IV-V above are well known or can be prepared according to procedures known in the art. Carboxylic acids of the type illustrated by the above formulae and processes for preparing their overbased metal salts are well known and disclosed, for example, in such U.S. Pat. Nos. as 2,197,832; 2,197,835; 2,252,662; 2,252,664; 2,714,092; 3,410,798 and 3,595,791 which are incorporated by reference herein for their disclosures of acids and methods of preparing overbased salts.

Component C may also be a borated complex of either an alkali overbased sulfonic acid or an alkaline overbased carboxylic acid such as described hereinabove. Borated complexes of this type may be prepared by heating the overbased sulfonic acid or overbased carboxylic acid with boric acid at about 50°–100° C., the number of equivalents of boric acid being roughly equal to the number of equivalents of alkali metal in the salt. U.S. Pat. No. 3,929,650 is incorporated by reference herein for its disclosure of borated complexes.

Another type of overbased carboxylate salt used in making (C) of this invention are those derived from alkenyl succinates of the general formula:

(VII)

wherein R* is as defined above in Formula IV. Such salts and means for making them are set forth in U.S. Pat. Nos. 3,271,130, 3,567,637 and 3,632,510, which are hereby incorporated by reference in this regard.

Other patents specifically describing techniques for making overbased salts of the hereinabove-described sulfonic acids, carboxylic acids, and mixtures of any two or more of these include U.S. Pat. Nos. 2,501,731; 2,616,904; 2,616,905; 2,616,906; 2,616,911; 2,616,924; 2,616,925; 2,617,049; 2,777,874; 3,027,325; 3,256,186; 3,282,835; 3,384,585; 3,373,108; 3,365,296; 3,342,733; 3,320,162; 3,312,618; 3,318,809; 3,471,403; 3,488,284; 3,595,790; and 3,629,109. The disclosures of these patents are hereby incorporated in this present specification for their disclosures in this regard as well as for their disclosure of specific suitable basic metal salts.

In the context of this invention, phenols are considered organic acids. Thus, overbased salts of phenols (generally known as phenates) are also useful in making (C) of this invention are well known to those skilled in the art. The phenols from which these phenates are formed are of the general formula:

(VIII)

wherein R*, n, Ar*, X and m have the same meaning and preferences are described hereinabove with reference to Formula IV. The same examples described with respect to Formula IV also apply.

A commonly available class of phenates are those made from phenols of the general formula:

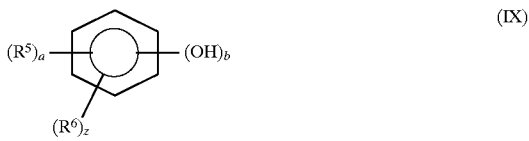
(IX)

wherein a is an integer of 1–3, b is of 1 or 2, z is 0 or 1, $R^5$ in Formula IX is a hydrocarbyl-based substituent having an average of from 4 to about 400 aliphatic carbon atoms and $R^6$ is selected from the group consisting of lower hydrocarbyl, lower alkoxyl, nitro, amino, cyano and halo groups.

One particular class of phenates for use in this invention are the overbased, Group IIA metal sulfurized phenates made by sulfurizing a phenol as described hereinabove with a sulfurizing agent such as sulfur, a sulfur halide, or sulfide or hydrosulfide salt. Techniques for making these sulfurized phenates are described in U.S. Pat. Nos. 2,680,096; 3,036,971; and 3,775,321 which are hereby incorporated by reference for their disclosures in this regard.

Other phenates that are useful are those that are made from phenols that have been linked through alkylene (e.g., methylene) bridges. These are made by reacting single or multi-ring phenols with aldehydes or ketones, typically, in the presence of an acid or basic catalyst. Such linked phenates as well as sulfurized phenates are described in detail in U.S. Pat. No. 3,350,038; particularly columns 6–8 thereof, which is hereby incorporated by reference for its disclosures in this regard.

Generally Group IIA overbased salts of the above-described carboxylic acids are typically useful in making (C) of this invention.

The method of preparing metal overbased compositions in this manner is illustrated by the following examples.

EXAMPLE C-1

Charged to a 5 liter flask is 834 parts (3 equivalents) of a commercial fatty acid (acid number of 200), 1500 parts mineral oil, 400 parts of an alcohol solution containing 60% isobutyl alcohol and 40% 3-methylbutyl alcohol and a 204 part solution of 4 parts calcium chloride dissolved in 200 parts water. The contents are heated to 45° C. and charged is 132 parts (3.57 equivalents) calcium hydroxide. The temperature is increased to reflux of 95° C. and held there for 1.5 hours. The contents are slowly dried to 150° C. At 45° C. is charged 100 parts of the previously mentioned alcohol solution followed by 90 parts (2.43 equivalents) calcium hydroxide and 390 parts methyl alcohol. After a ten minute digestion period $CO_2$ is blown below the surface at one cubic foot per hour at 50°–55° C. until a neutralization number to phenolphthalein of 6 is obtained. The contents are stripped to 160° C. while blowing with nitrogen at 1.5 cubic feet per hour. The contents are then filtered using a diatomaceous filter aid to give a product containing 59% oil. Analyses: % $CaSO_4$ ash 15.73; neutralization number to bromophenol blue 130.

EXAMPLE C-2

A solution of 780 parts (1 equivalent) of an alkylated benzenesulfonic acid and 119 parts (0.2 equivalents) of a polybutenyl succinic anhydride in 442 parts of mineral oil is mixed with 800 parts (20 equivalents) of sodium hydroxide and 704 parts (22 equivalents) of methanol. The mixture is blown with carbon dioxide at 7 cfh. for 11 minutes as the temperature slowly increases to 95° C. The rate of carbon dioxide flow is reduced to 6 cfh. and the temperature decreases slowly to 88° C. over about 40 minutes. The rate of carbon dioxide flow is reduced to 5 cfh. for about 35 minutes and the temperature slowly decreases to 73° C. The volatile materials are stripped by blowing nitrogen through the carbonated mixture at 2 cfh. for 105 minutes as the temperature is slowly increased to 160° C. After stripping is completed, the mixture is held at 160° C. for an additional 45 minutes and then filtered to yield an oil solution of the desired basic sodium sulfonate having a metal ratio of about 19.75. This solution contains 18.0% oil.

EXAMPLE C-3

A reaction mixture comprising about 512 parts by weight of a mineral oil solution containing about 0.5 equivalent of a substantially neutral magnesium salt of an alkylated salicylic acid wherein the alkyl group has an average of about 18 aliphatic carbon atoms and about 30 parts by weight of an oil mixture containing about 0.037 equivalent of an alkylated benzenesulfonic acid together with about 15 parts by weight (about 0.67 equivalent) of a magnesium oxide and about 250 parts by weight of xylene is added to a flask and heated to a temperature of about 60° C. to 70° C. The reaction mass is subsequently heated to about 85° C. and approximately 60 parts by weight of water are added. The reaction mass is held at a reflux temperature of about 95° C. to 100° C. for about 1 ½ hours and subsequently stripped at a temperature of 155° C.–160° C., under a vacuum, and filtered. The filtrate comprises the basic carboxylic magnesium salt characterized by a sulfated ash content of 12.35% (ASTM D-874, IP 163), indicating that the salt contains 200% of the stoichiometrically equivalent amount of magnesium.

EXAMPLE C-4a

Charged to a 12 liter flask is 5000 parts (18.79 equivalents) of a propylene tetramer phenol. The contents are heated with stirring to 80° C. and charged are 907 parts (28.34 moles) sulfur and 296 parts (8 equivalents) Ca(OH)$_2$. At 100° C. 111.5 parts ethylene glycol is added. The contents are heated to 185° C. with nitrogen blowing at 1 cubic foot per hour. By-product H$_2$S is trapped in aqueous sodium hydroxide and a sodium hypochlorite solution. The contents are held at 185° C. for 15 hours with continuous nitrogen blowing. Mineral oil (1228 parts) is added and the obtained product has a % sulfur of 8.81.

EXAMPLE C-4b

To a 3 liter flask is added 144 parts ethylene glycol, 182 parts decyl alcohol, 90 parts (0.088 equivalents) of a neutral calcium petroleum sulfonate and 338 parts mineral oil. The contents are heated to 100° C. and 752 parts (2 equivalents based on theory phenol) of the material of Example C-4a is added. After a 0.1 hour mixing period, added is 230 parts (6.2 equivalents) of Ca(OH)$_2$. The contents are heated to 163° C. with nitrogen blowing at 1 cubic foot per hour and water is azeotroped out of the reaction mixture. Carbon dioxide is then blown below the surface at 1 cubic foot per hour for 1.7 hours. The contents are stripped to 220° C. with nitrogen blowing at 2 cubic feet per hour. The stripping is completed under vacuum at 220° C. and 40 mm mercury. The contents are then filtered using a filtering aid. Analyses: % CaSO$_4$ ash 32.4; % sulfur 3.21; total base number to bromophenol blue 269.

EXAMPLE C-5a

A calcium mahogany sulfonate is prepared by double decomposition of a 60% oil solution of 750 parts of sodium mahogany sulfonate with the solution of 67 parts of calcium chloride and 63 parts of water. The reaction mass is heated for four hours at 90° to 100° C. to affect the conversion of the sodium mahogany sulfonate to calcium mahogany sulfonate. Then 54 parts of calcium hydroxide is added and the material is heated to 150° C. over a period of five hours. When the material has cooled to 40° C., 98 parts of methanol is added and 152 parts of carbon dioxide is introduced over a period of 20 hours at 42°–43° C. Water and alcohol are then removed by heating the mass to 150° C. The residue in the reaction vessel is diluted with 100 parts of mineral oil. The filtered oil solution and the desired carbonated calcium sulfonate overbased material shows the following analysis: sulfate ash content, 16.2%; and a metal ratio of 2.40.

EXAMPLE C-5b

A mixture comprising 1100 parts of the overbased material of Example C-5a, 58 parts of a calcium phenate prepared as indicated below (0.065 equivalent), 553 parts of mineral oil, 110 parts of calcium hydroxide (2.97 equivalents), 194 parts of methanol, 97 parts of an alcohol solution containing 60% isobutyl alcohol and 40% 3-methylbutyl alcohol and 1.9 parts calcium chloride dissolved in 6.1 parts water is stirred vigorously at 40° C. and carbon dioxide is introduced at 40°–50° C. at 1 cfh until a direct base number of between 40–50 is obtained. Thereafter, three additional portions of calcium hydroxide, each amounting to 103 parts each are added and each such addition is followed by the introduction of carbon dioxide as previously illustrated. The carbonated reaction mixture is then heated to 150° C. under a nitrogen atmosphere to remove alcohol and any by-product water. The residue in the reaction vessel is then filtered. The filtrate, an oil solution of the desired carbonated calcium sulfonate overbased material of high metal ratio shows the following analysis: % sulfate ash 38.91; total base number 302); and a metal ratio of 12.67.

The calcium phenate used above is prepared by adding 2550 parts of mineral oil, 960 parts (5 moles) of heptylphenol, and 50 parts of water into a reaction vessel and stirring at 25° C. The mixture is heated to 40° C. and 7 parts of calcium hydroxide and 231 parts (7 moles) of 91% commercial paraformaldehyde is added over a period of one hour. The contents are heated to 80° C. and 200 additional parts of calcium hydroxide (making a total of 207 parts or 5 moles) is added over a period of one hour at 80°–90° C. The contents are heated to 150° C. and maintained at that temperature for twelve hours while nitrogen is blown through the mixture to assist in the removal of water. If foaming is encountered, a few drops of polymerized dimethylsilicone foam inhibitor may be added to control the foaming. The reaction mass is then filtered. The filtrate, a 33.6% oil solution of the desired calcium phenate of heptaphenolformaldehyde condensation product is found to contain 7.56% sulfate ash.

EXAMPLE C-6

A solution of 639 parts (1.08 equivalents) of an alkylated benzenesulfonic acid, 861 parts mineral oil, 113 parts (0.20 equivalents) of a polybutenyl succinic anhydride and 1157 parts xylene is added to a 5 liter flask. The contents are heated to 46° C. and added are 131 parts (6.55 equivalents) of magnesium oxide and 54 parts (0.9 equivalents) of acetic acid. This is followed by the addition of 47 parts methanol and 88 parts water. A 20° C. exotherm occurs and after the contents are cooled to 52° C., $CO_2$ is blown below the surface at 2 cubic feet per hour for 1 hour. A second increment of the same size of magnesium oxide, methanol and water is added and carbonation at 2 cubic feet per hour continues for another hour. The final increment of magnesium oxide, methanol and water of the same size is added. The carbonation rate of 2 cubic feet per hour is conducted for 1.5 hours. The contents are then stripped to 165° C. while blowing with $CO_2$ at 2 cubic feet per hour after which the contents are vacuum stripped to 170° C. at 15 mm mercury. The contents are then filtered using a filter aid to give a product having the following analyses: total base number 400; % sulfur 1.76; % $MgSO_4$ ash 44.9.

The Amine Composition

The amines which are reacted with component (D) to form the amine salts may be ammonia, or a primary, secondary or tertiary amine, or mixtures thereof as represented by the formula $$R^7R^8R^9N$$

wherein $R^7$, $R^8$ and $R^9$ are each independently hydrogen, hydrocarbyl, aminohydrocarbyl hydroxyhydrocarbyl, aminohydrocarbyl or hydroxyhydrocarbyloxy hydrocarbyl groups, or $R^7$ and $R^8$ may be hydrocarbyl groups joined together to form a ring structure including the nitrogen atom and optionally additional hetero atoms such as nitrogen, oxygen, phosphorus or sulfur. Generally, the hydrocarbyl groups will contain up to about 150 carbon atoms and will more often be aliphatic hydrocarbyl groups containing from about 1 to about 30 carbon atoms.

In another embodiment the amine salt is derived from an acylated amine prepared by the reaction of a hydrocarbon-substituted carboxylic acid producing compound (e.g., a succinic acid producing compound) with at least about one-half of an equivalent, per equivalent of acid-producing compound, of an amine containing at least one hydrogen attached to a nitrogen atom.

In one embodiment, the hydrocarbyl amines which are useful in preparing the amine salts of the present invention are primary hydrocarbyl amines containing from about 2 to about 30 carbon atoms in the hydrocarbyl group, and more preferably from about 4 to about 20 carbon atoms in the hydrocarbyl group. The hydrocarbyl group may be saturated or unsaturated. Representative examples of primary saturated amines are the lower alkyl amines such as methyl amine, ethyl amine, n-propyl amine, n-butyl amine, n-amyl amine, n-hexyl amine; those known as aliphatic primary fatty amines and commercially known as "Armeen" primary amines (products available from Armak Chemicals, Chicago, Ill.). Typical fatty amines include alkyl amines such as n-hexylamine, n-octylamine, n-decylamine, n-dodecylamine, n-tetradecylamine, n-pentadecylamine, n-hexadecylamine, n-octadecylamine (stearyl amine), etc. These Armeen primary amines are available in both distilled and technical grades. While the distilled grade will provide a purer reaction product, the desirable amides and imides will form in reactions with the amines of technical grade. Also suitable are mixed fatty amines such as Armak's Armeen-C, Armeen-O, Armeen-OL, Armeen-T, Armeen-HT, Armeen S and Armeen SD.

In another embodiment, the amine salts of the additives of this invention are those derived from tertiary-aliphatic primary amines having at least about 4 carbon atoms in the alkyl group. For the most part, they are derived from alkyl amines having a total of less than about 30 carbon atoms in the alkyl group.

Usually the tertiary aliphatic primary amines are monoamines represented by the formula

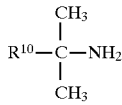

wherein $R^{10}$ is a hydrocarbyl group containing from one to about 30 carbon atoms. Such amines are illustrated by tertiary-butyl amine, tertiary-hexyl primary amine, 1-methyl-1-amino-cyclohexane, tertiary-octyl primary amine, tertiary-decyl primary amine, tertiary-dodecyl primary amine, tertiary-tetradecyl primary amine, tertiary-hexadecyl primary amine, tertiary-octadecyl primary amine, tertiary-tetracosanyl primary amine, tertiary-octacosanyl primary amine.

Mixtures of amines are also useful for the purposes of this invention. Illustrative of amine mixtures of this type are "Primene 81R" which is a mixture of $C_{11}$–$C_{14}$ tertiary alkyl primary amines and "Primene JM-T" which is a similar mixture of $C_{18}$–$C_{22}$ tertiary alkyl primary amines (both are available from Rohm and Haas Company). The tertiary alkyl primary amines and methods for their preparation are well known to those of ordinary skill in the art and, therefore, further discussion is unnecessary. The tertiary alkyl primary amine useful for the purposes of this invention and methods for their preparation are described in U.S. Pat. No. 2,945,749 which is hereby incorporated by reference for its teaching in this regard.

Primary amines in which the hydrocarbon chain comprises olefinic unsaturation also are quite useful. Thus, the $R^7$ group may contain one or more olefinic unsaturations depending on the length of the chain, usually no more than one double bond per 10 carbon atoms. Representative amines are dodecenylamine, myristoleylamine, palmitoleylamine, oleylamine and linoleylamine. Such unsaturated amines also are available under the Armeen tradename.

Secondary amines include dialkylamines having two of the above alkyl groups including such commercial fatty secondary amines as Armeen 2C and Armeen HT, and also mixed dialkylamines where, for example, $R^7$ is a fatty amine and $R^8$ may be a lower alkyl group (1–9 carbon atoms) such as methyl, ethyl, n-propyl, i-propyl, butyl, etc., or $R^8$ may be an alkyl group bearing other non-reactive or polar substituents (CN, alkyl, carbalkoxy, amide, ether, thioether, halo, sulfoxide, sulfone) such that the essentially hydrocarbon character of the group is not destroyed. The fatty polyamine diamines include mono- or dialkyl, symmetrical or asymmetrical ethylene diamines, propane diamines (1,2, or 1,3), and polyamine analogs of the above. Suitable commercial fatty polyamines are "Duomeen C" (N-coco-1,3-diaminopropane), "Duomeen S" (N-soya-1,3-diaminopropane), "Duomeen T" (N-tallow-1,3-diaminopropane), or "Duomeen O" (N-oleyl-1,3-diaminopropane). "Duomeens" are commercially available diamines described in Product Data Bulletin No. 7-0R1 of Armak Chemical Co., Chicago, Ill. In another embodiment, the secondary amines may be cyclic amines such as piperidine, piperazine, morpholine, etc.

Other primary amines useful in the preparation of the amine salts and are the primary ether amines $R^{11}OR^{12}NH_2$ wherein $R^{12}$ is a divalent alkylene group having 2 to 6 carbon atoms and $R^{11}$ is a hydrocarbyl group of bout 5 to about 150 carbon atoms. These primary ether amines are generally prepared by the reaction of an alcohol $R^{11}$ with an unsaturated nitrile. The $R^{11}$ group of the alcohol can be a hydrocarbon-based group having up to about 150 carbon atoms. Typically, and for efficiency and economy, the alcohol is a linear or branched aliphatic alcohol with $R^{11}$ having up to about 50 carbon atoms, preferably up to 26 carbon atoms and most preferably $R^{11}$ has from 6 to 20 carbon atoms. The nitrile reactant can have from 2 to 6 carbon atoms with acrylonitrile being most preferred. Ether amines are known commercial products which are available under the name SURFAM™ produced and marketed by Mars Chemical Company, Atlanta, Ga. Typical of such amines are those having from about 150 to about 400 molecular weight. Preferred etheramines are exemplified by those identified as SURFAM P14AB (branched $C_{14}$), SURFAM P16A (linear $C_{16}$), SURFAM P17AB (branched $C_{17}$). The carbon chain lengths (i.e., $C_{14}$, etc.) of the SURFAMS described above and used hereinafter are approximate and include the oxygen ether linkage. For example, $AC_{14}$ SURFAM would have the following general formula

The amines used to form the amine salts may be hydroxyhydrocarbyl amines. That is $R^7$, $R^8$ and/or $R^9$ may be hydroxyhydrocarbyl or hydroxyhydrocarbyloxyhydrocarbyl groups. In one embodiment, these hydroxyhydrocarbyl amines can be represented by the formula

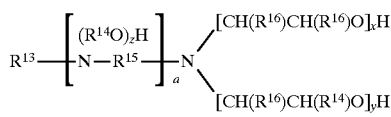

wherein $R^{13}$ is a hydrocarbyl group generally containing from about 6 to about 30 carbon atoms, $R^{14}$ is an ethylene or propylene group, $R^{15}$ is an alkylene group containing up to about 5 carbon atoms, a is zero or one, each $R^{16}$ is hydrogen or a lower alkyl group, and x, y and z are each independently integers from zero to about 10, at least one of x, y and z being at least 1.

The above hydroxyhydrocarbyl amines can be prepared by techniques well known in the art, and many such hydroxyhydrocarbyl amines are commercially available. They may be prepared, for example, by reaction of primary amines containing at least 6 carbon atoms with various amounts of alkylene oxides such as ethylene oxide, propylene oxide, etc. The primary amines may be single amines or mixtures of amines such as obtained by the hydrolysis of fatty oils such as tallow oils, sperm oils, coconut oils, etc. Specific examples of fatty acid amines containing from about 6 to about 30 carbon atoms include saturated as well as unsaturated aliphatic amines such as octyl amine, decyl amine, lauryl amine, stearyl amine, oleyl amine, myristyl amine, palmityl amine, dodecyl amine, and octadecyl amine.

The useful hydroxyhydrocarbyl amines where a in the above formula is zero include 2-hydroxyethylhexylamine, 2-hydroxyethyloctylamine, 2-hydroxyethyldodecylamine, 2-hydroxyethyltetradecylamine, 2-hydroxyethylpentadecylamine, 2-hydroxyethyleicosylamine, 2-hydroxyethyltriacontylamine, 2-hydroxyethyloleylamine, 2-hydroxyethyltallowamine, 2-hydroxyethylsoyamine, bis-(2-hydroxyethyl)hexylamine, bis (2-hydroxyethyl)octylamine, bis (2-hydroxyethyl)dodecylamine, bis(2-hydroxyethyl)-tetradecylamine, bis(2-hydroxyethyl)pentadecylamine, bis(2-hydroxyethyl)eicosylamine, bis(2-hydroxyethyl)-triacontylamine, bis(2-hydroxyethyl)oleylamine, bis(2-hydroxyethyl)tallowamine, bis(2-hydroxyethyl)soyamine, 2-hydroxylpropylhexylamine, 2-hydroxypropyloctylamine, 2-hydroxypropyldodecylamine, 2-hydroxypropyltetradecylamine, 2-hydroxypropylpentadecylamine, 2-hydroxypropyleicosylamine, 2-hydroxypropyltriacontylamine, 2-hydroxypropyloleylamine, 2-hydroxypropyltallowamine, 2-hydroxypropylsoyamine, bis(2-hydroxypropyl) hexylamine, bis(2-hydroxypropyl)octylamine, bis (2-hydroxypropyl)dodecylamine, bis(2-hydroxypropyl) tetradecylamine, bis(2-hydroxypropyl)pentadecylamine, bis (2-hydroxypropyl)eicosylamine, bis(2-hydroxypropyl) triacontylamine, bis(2-hydroxypropyl)oleylamine, bis(2-hydroxypropyl)tallowamine, bis(2-hydroxypropyl) soyamine and mixtures thereof. Also included are the comparable members wherein in the above formula at least one of x and y is at least 2, as for example, 2-hydroxyethoxyethylhexylamine.

A number of hydroxyhydrocarbyl amines wherein a is zero are available from the Armak Chemical Division of Akzona, Inc., Chicago, Ill., under the general trade designation "Ethomeen" and "Propomeen". Specific examples of such products include "Ethomeen C/15" which is an ethylene oxide condensate of a coconut fatty acid containing about 5 moles of ethylene oxide; "Ethomeen C/20" and "C/25" which also are ethylene oxide condensation products from coconut fatty acid containing about 10 and 15 moles of ethylene oxide respectively; "Ethomeen O/12" which is an ethylene oxide condensation product of oleyl amine containing about 2 moles of ethylene oxide per mole of amine. "Ethomeen S/15" and "S/20" which are ethylene oxide condensation products with stearyl amine containing about 5 and 10 moles of ethylene oxide per mole of amine respectively; and "Ethomeen T/12, T/15" and "T/25" which are ethylene oxide condensation products of tallow amine containing about 2, 5 and 15 moles of ethylene oxide per mole of amine respectively. "Propomeen O/12" is the condensation product of one mole of oleyl amine with 2 moles propylene oxide.

Commercially available examples of alkoxylated amines where a is 1 include "Ethoduomeen T/13" and "T/20" which are ethylene oxide condensation products of N-tallow trimethylene diamine containing 3 and 10 moles of ethylene oxide per mole of diamine, respectively.

The Metal Oxide and Metal Hydroxide

The metal oxide and hydroxide having utility as the neutralizing agent are the oxides and hydroxides of Group I and Group II metals of the Periodic Table. These metals specifically are lithium, sodium, potassium, magnesium, calcium, strontium and zinc.

As stated above, component (D) as well as the trithiane are formed from components (A) and (B). This is accomplished by admixing components (A) and (B) at a temperature of from ambient up to about 150° C. and observing via infrared the decrease of the carbonyl (C=O) moiety. The following examples are illustrative of the process of the instant invention and are directed to the formation of the trithiane and component (D). Unless otherwise indicated, all temperatures are in centigrade.

EXAMPLE 1

Charged to a three-liter, four-necked flask is 769.3 parts (six moles) 2-ethylhexanal and the contents are heated to 80° C. while purging with nitrogen at 0.2 cubic feet per hour. Over a one hour time period is added 1140 parts (three moles) of O,O-diisooctyl hydrogen phosphorodithioate, corresponding to the formula

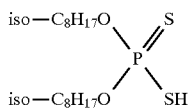

The contents are heated up to 125° C. over two and a half hours and held at this temperature for one and a half hours. At 85° C. the contents are vacuum stripped at 15 mm mercury. Obtained is 1894 parts of product having a neutralization number to bromophenol blue of 79 and a neutralization number to phenophthalein of 111. The product of this example is a trithiane wherein $R^1$ is $C_7H_{15}$ and component (D).

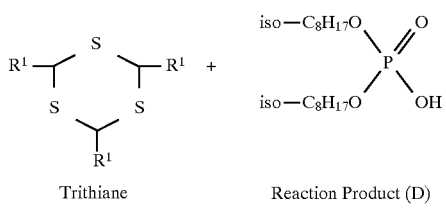

Trithiane          Reaction Product (D)

EXAMPLE 2

The procedure of Example 1 is repeated except that the mole ratio of 2-ethylhexanal and O,O-diisooctyl hydrogen phosphorodithioate is 1:1 and not 2:1. Obtained is the trithiane of Example 1 and component (D) of the following structure:

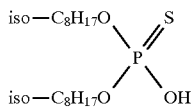

Component (D) is reacted with the neutralizing agent to form the salt. Salt formation occurs at a temperature of from ambient up to about 75° C. For each equivalent of component (D) (equivalency based on phosphorus) from about 0.75 up to about 3.0 equivalents of neutralizing agent, preferably from about 0.75 to about 2.5, and most preferably from about 0.75 to about 2.0 equivalents (based on neutralization number) is employed. The neutralizing agent may be added to the filtered trithiane-component (D) mixture or may be added after the formation but before the filtration of the trithiane-component (D). In Examples 3–7, the former is demonstrated and in the subsequent Examples 8–12 the latter is demonstrated.

EXAMPLE 3

To a two-liter, four-necked flask is added 568 parts (0.9 equivalents) of the composition of Example 1. The contents are stirred while purging with nitrogen at 0.2 cubic feet per hour and at 30° C. 449 parts (2.16 equivalents of the composition of Example C-1 is added. The contents are heated to 40° C. and held there for 30 minutes and then stripped to 80° C. at 10 mm mercury. Residue is product. Analyses: % sulfur 3.95; % phosphorus 1.84; % calcium 3.06; neutralization number bromophenol blue 43.5.

EXAMPLE 4

Following the procedure of Example 3, 158 parts (0.25 equivalents) of the composition of Example 1 is added to a reaction vessel along with 56 parts (0.30 equivalents) of the compositions of Example C-5b and 50 ml. toluene. The contents are heated to 30° C. at which time an exotherm carries the temperature to 40° C. The contents are stripped to 80° C. at 10 mm mercury. The salt has the following analyses: % sulfur 8.38; % phosphorus 3.74; % calcium 3.25; neutralization number to bromophenol blue 7.9.

EXAMPLE 5

The procedure of Example 4 is repeated except that 92.4 parts (0.30 equivalents) of the composition of Example C-4b is used in place of the composition of Example C-5b. The obtained salt has the following analyses: % sulfur 7.71; % phosphorus 3.16; % calcium 3.67; D664B base number 13.0.

EXAMPLE 6

The procedure of Example 4 is repeated except that 42.1 parts (0.30 equivalents) of the composition of Example C-6 is used in place of the composition of Example C-5b. The obtained salt has the following analyses: % sulfur 8.65; % phosphorus 3.69; % magnesium 1.99; D664B base number 2.9.

EXAMPLE 7

The procedure of Example 4 is repeated except that 38.3 parts (0.30 equivalents) of the composition of Example C-2 is used in place of the composition of Example C-5b. The obtained salt has the following analyses: % sulfur 8.61; % phosphorus 4.01; % sodium 3.74; D664B base number 58.2.

EXAMPLE 8

Within this example, the aldehyde: phosphorus acid, molar ratio is 1:1.

Charged to a one-liter flask is 128.2 parts (1.0 mole) 2-ethylhexanal and 380 parts (1 mole) O,O-diisooctyl hydrogen phosphorodithioate. The contents are heated to 80° C. while purging with nitrogen at 0.2 cubic feet per hour and held at this temperature for one hour. The temperature is increased to 150° C. over four hours and held at this temperature for five hours. At 40° C. 122 parts (0.639 moles) Primene 81R amine is added and the temperature is maintained at 40° C. The obtained salt has the following analyses: % sulfur 9.35; % phosphorus 4.90; % nitrogen 1.45; neutralization number to phenolphthalein 70.6.

EXAMPLE 9

Within this example, the aldehyde:phosphorus acid molar ratio is 2:1.

Charged to a one-liter flask is 192.3 parts (1.5 moles) 2-ethylhexanal and 270.8 parts (0.75 moles) O,O-diisooctyl hydrogen phosphorodithioate. The contents are heated to 125 at 20 mm mercury and held there for one hour. At 40° C. 125 parts (0.654 moles) Primene 81R is added and the temperature is maintained at 40° C. The obtained salt has the following analyses: % sulfur 7.63; % phosphorus 3.71; % nitrogen 1.58; neutralization number to bromophenol blue 2.4.

EXAMPLE 10

A dithiodiphosphoric acid is prepared by reacting $P_2S_5$ with an alcoholic mixture containing 60% 4-methyl-sec-amyl alcohol and 40% isopropyl alcohol.

Charged to a two-liter flask is 288 parts (4 moles) isobutyraldehyde and heated to 50° C. where 582 parts (2 moles)

of the dithiophosphoric acid is added. The contents are heated to 125° C. and held there for 2 hours. The contents are then cooled to 80° C. at 25 mm mercury. At 60° C. 312 parts (1.63 moles) Primene 81R is added and the temperature is maintained at 60° C. The obtained salt has the following analyses: % sulfur 10.6; % phosphorus 5.06; % nitrogen 2.28; neutralization number to bromophenol blue 5.

EXAMPLE 11

A dithiophosphoric acid is prepared by reacting $P_2S_5$ with 4-methyl-sec-amyl alcohol.

Charged to a one-liter flask 192 parts (1.5 moles) 2-ethylhexanal and heated to 80° C. where 246 parts (0.75 moles) of the above dithiophosphoric acid is added. The contents are heated to 125° C. and held there for 1.5 hours. The contents are then stripped to 80° C. at 15 mm mercury. At 40° C. 125 parts (0.65 moles) Primene 81R is added and the temperature is maintained at 40° C. The obtained salt has the following analyses: % sulfur 8.66; % phosphorus 4.09; % nitrogen 1.68; neutralization number to bromophenol blue 3.

EXAMPLE 12

Charged to a one-liter flask is 144 parts (2.0 moles) isobutyraldehyde and heated to 50° C. where 400 parts O,O-diisooctyl hydrogen phosphorodithioate is added. The contents are heated to 125° C., maintained at this temperature for 1.5 hours, then cooled to 80° C. at 15 mm mercury. At 60° C. 172 parts (0.90 moles) Primene 81R is added and the temperature is maintained at 60° C. The obtained salt has the following analyses: % sulfur 9.19; % phosphorus 4.85; % nitrogen 1.86; neutralization number to bromophenol blue 4.

The additive formed by the process of the present invention has been found to be a useful extreme pressure agent for lubricating compositions. The additive of the present invention may also find use as additives for other such functional fluids as automatic transmission fluids and hydraulic fluids.

The additive formed by the process of the invention may be formulated with a lubricating oil or an automatic transmission fluid or the like by the direct blending of the additive with the particular oil or functional fluid to be formulated. The lubricating oil or other functional fluid may also be formulated with compounds of the present invention in the form of a concentrate. Such a concentrate may be prepared by adding 1% to about 99% by weight of the reaction product of components A and B or the reaction product of components A and B with component C to a substantially inert, normally liquid organic diluent or solvent such as benzene, toluene, xylene, petroleum naphtha, mineral oil, ethyleneglycol-mono-methylether or the like.

The amount of this additive formulated with a particular lubricant may vary over a wide range and must be an amount to effectively impart extreme pressure properties in the lubricant. As a preferred amount, the additive may range from 0.01 weight percent to about 10 weight percent of the formulated lubricant. In a most preferred embodiment, the amount may range from about 0.1 weight percent to about 5 weight percent of the formulated lubricant.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A process for the preparation of an extreme pressure additive comprising:

reacting (A) $R^1CHO$ and

at an (A):(B) molar ratio of 1:1 and at a temperature of from ambient up to about 150° C. forming

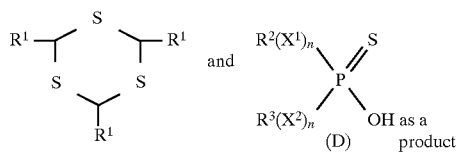

or at an (A):(B) molar ratio of 2:1 and at a temperature of from ambient up to about 150° C. forming

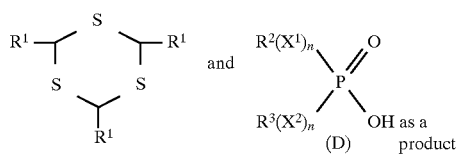

wherein $R^1$ is

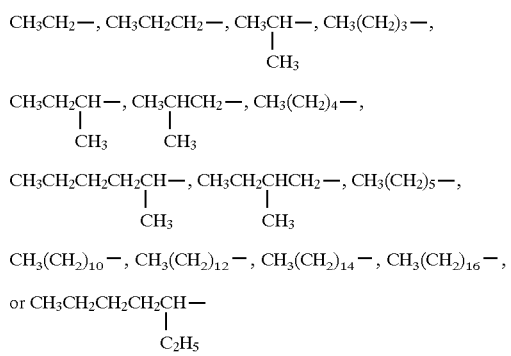

$R^2$ and $R^3$ are each independently a hydrocarbyl group containing from 1 to about 30 carbon atoms, $X^1$ and $X^2$ are each independently oxygen or sulfur and n is independently zero or one.

2. The process according to claim 1 wherein $R^1$ is

3. The process according to claim 2 wherein the hydrocarbyl groups $R^2$ and $R^3$ independently contain from 1 to about 12 carbon atoms.

4. The process according to claim 3 wherein $X^1$ and $X^2$ are both oxygen and n is 1.

5. A process for the preparation of an extreme pressure additive comprising:

reacting (A) $R^1CHO$ and

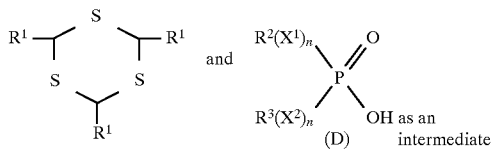

at an (A):(B) molar ratio of 1:1 and at a temperature of from ambient up to about 150° C. forming

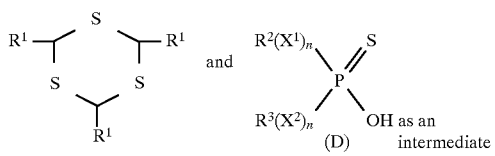

at an (A):(B) molar ratio of 2:1 and at a temperature of from ambient up to about 150° C. forming

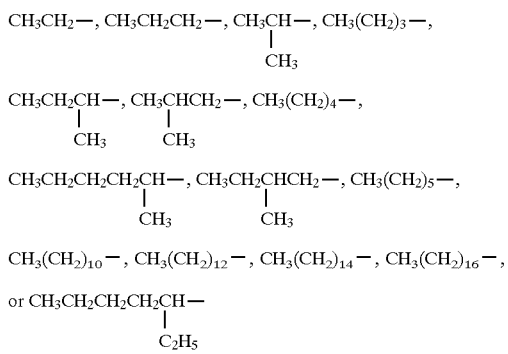

wherein $R^1$ is $CH_3CH_2-$, $CH_3CH_2CH_2-$, $CH_3CH-$, $CH_3(CH_2)_3-$,
$\qquad\qquad\qquad\qquad\qquad\ \ \ |$
$\qquad\qquad\qquad\qquad\qquad CH_3$ $CH_3CH_2CH-$, $CH_3CHCH_2-$, $CH_3(CH_2)_4-$,
$\quad\ \ \ |\qquad\qquad\ \ |$
$\quad\ \ CH_3\qquad\quad\ CH_3$ $CH_3CH_2CH_2CH_2CH-$, $CH_3CH_2CHCH_2-$, $CH_3(CH_2)_5-$,
$\qquad\qquad\qquad\ |\qquad\qquad\qquad\ |$
$\qquad\qquad\qquad CH_3\qquad\qquad\quad CH_3$ $CH_3(CH_2)_{10}-$, $CH_3(CH_2)_{12}-$, $CH_3(CH_2)_{14}-$, $CH_3(CH_2)_{16}-$, or $CH_3CH_2CH_2CH_2CH-$
$\qquad\qquad\qquad\quad |$
$\qquad\qquad\qquad\ C_2H_5$ $R^2$ and $R^3$ are each independently a hydrocarbyl group containing from 1 to about 30 carbon atoms, $X^1$ and $X^2$ are each independently oxygen or sulfur, n is independently zero or one, and reacting either said intermediate with a neutralizing agent at a temperature of from ambient up to about 75° C. comprising a metal overbased composition, an amine of the structure $R^4R^5R^6N$ wherein $R^4$, $R^5$ and $R^6$ are each independently hydrogen or a hydrocarbyl group containing from 1 to about 30 carbon atoms, metal oxide, metal hydroxides or mixtures of metal oxides and metal hydroxides wherein for each equivalent of (D) from about 0.75 up to about 3.0 equivalents of neutralizing agent is employed.

6. The process according to claim 5 wherein $R^1$ is $CH_3CH-$
$\quad\ |$
$\ \ CH_3$ 7. The process according to claim 6 wherein the hydrocarbyl groups $R^2$ and $R^3$ independently contain from 1 to about 12 carbon atoms.

8. The process according to claim 7 wherein $X^1$ and $X^2$ are both oxygen and n is 1.

9. The process according to claim 5 wherein the neutralizing agent (C) is a metal overbased composition.

10. The process of claim 9 wherein (C) is a metal overbased sulfonate derived from an alkylated aryl sulfonic acid wherein the alkyl group has at least 15 aliphatic carbon atoms.

11. The process of claim 10 wherein the metal is an alkali or alkaline earth metal.

12. The process of claim 11 wherein the alkaline earth metal is calcium or magnesium.

13. The process of claim 11 wherein the alkali metal is sodium.

14. The process of claim 9 wherein (C) is a metal overbased carboxylate derived from fatty acids having at least 12 aliphatic carbon atoms.

15. The process of claim 14 wherein the metal is calcium or magnesium.

16. The process of claim 9 wherein (C) is a metal overbased phenate derived from the reaction of an alkylated phenol wherein the alkyl group has at least 6 aliphatic carbon atoms with formaldehyde.

17. The process of claim 16 wherein the metal is calcium or magnesium.

18. The process of claim 16 wherein the phenate is derived from the reaction of an alkylated phenol wherein the alkyl groups has at least 6 aliphatic carbon atoms with a sulfurization agent.

19. The process of claim 18 wherein the metal is calcium or magnesium.

20. The process of claim 16 wherein the phenate is derived from the reaction of an alkylated phenol having at least 6 aliphatic carbon atoms with a sulfurization agent and formaldehyde.

21. The process of claim 20 wherein the metal is calcium or magnesium.

22. The process according to claim 5 wherein the neutralizing agent (C) is an amine of the structure $R^4R^5R^6N$ wherein $R^4$, $R^5$ and $R^6$ are each independently hydrogen or a hydrocarbyl group containing from 1 to about 30 carbon atoms.

23. The process according to claim 22 wherein $R^4$ and $R^5$ are hydrogen and $R^6$ is a hydrocarbyl containing from 1 to about 18 carbon atoms.

24. The process according to claim 5 wherein the neutralizing agent (C) is selected from the group consisting of metal oxides, metal hydroxides and mixtures thereof.

25. The process according to claim 24 wherein the metals are selected from the group consisting of alkali metals, alkaline earth metals, transition metals, aluminum, tin, silicon and boron and combinations thereof.

26. The process according to claim 25 wherein the alkali metals are selected from the group consisting of lithium, sodium and potassium.

27. The process according to claim 25 wherein the alkaline earth metals are selected from the group consisting of magnesium, calcium and barium.

28. The process according to claim 25 wherein the transition metals are selected from the group consisting of zinc, molybdenum, manganese, nickel, cobalt, copper, titanium, vanadium, tungsten, zirconium, iron and combinations thereof.

29. A concentrate for formulating lubricating compositions comprising from about 1 percent to about 99 percent by weight of the extreme pressure additive of claim 1 with the balance being a substantially inert, normally liquid organic diluent or solvent.

30. A concentrate for formulating lubricating compositions comprising from about 1 percent to about 99 percent by weight of the extreme pressure additive of claim 5 with the balance being a substantially inert, normally liquid organic diluent or solvent.

31. A lubricant composition, comprising from about 0.01 percent to about 10 percent by weight of the extreme pressure additive obtained through the process of claim 1 with the balance being a substantially inert, normally liquid organic diluent or solvent.

32. A lubricant composition comprising from about 0.01 percent to about 10 percent by weight of the extreme pressure additive obtained through the process of claim 5 with the balance being a substantially inert, normally liquid organic diluent or solvent.

* * * * *